(12) United States Patent
Murphy et al.

(10) Patent No.: US 6,730,675 B2
(45) Date of Patent: May 4, 2004

(54) COMPOUNDS AND METHODS FOR THE TREATMENT OF PAIN

(75) Inventors: Megan Murphy, Wilmington, DE (US); Rebecca Ann Urbanek, Wilmington, DE (US); Wenhua Xiao, Montreal (CA); Gary Banks Steelman, Wilmington, DE (US); Dean Gordon Brown, Wilmington, DE (US); Thomas Michael Bare, West Chester, PA (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/168,762

(22) Filed: Feb. 12, 2003

(65) Prior Publication Data

US 2003/0153572 A1 Aug. 14, 2003

Related U.S. Application Data

(60) Provisional application No. 60/171,906, filed on Dec. 23, 1999, and provisional application No. 60/236,786, filed on Sep. 29, 2000.

(51) Int. Cl.⁷ .................. C07D 471/04; A61K 31/5025
(52) U.S. Cl. ....................... 514/248; 544/234
(58) Field of Search ............................ 544/234; 514/248

(56) References Cited

FOREIGN PATENT DOCUMENTS

EP          0736531 A1     10/1996
WO        WO 9511244 A1   4/1995

*Primary Examiner*—Bruck Kifle
(74) *Attorney, Agent, or Firm*—Kenneth F. Mitchell

(57) ABSTRACT

Compounds according to structural diagram I are disclosed;

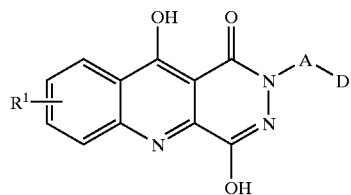

wherein $R^1$, A and D are as defined in the specification. Also disclosed are methods for treating pain comprising administration of a pain-ameliorating effective amount of a compound in accord with structural diagram I and pharmaceutical compositions comprising a pain-ameliorating effective amount of a compound in accord with structural diagram I.

10 Claims, No Drawings

COMPOUNDS AND METHODS FOR THE TREATMENT OF PAIN

This is a filing under Section 371 of PCT Application PCT/SE00/02609 filed Dec. 19, 2000, pending, which has a right to priority under the Paris Convention of U.S. Provisional Application Nos. 60/171,906, filed Dec. 23, 1999 and 60/236,786 filed Sep. 29, 2000.

FIELD OF THE INVENTION

This invention relates to the treatment or prevention of pain or nociception.

RELATED ART

Pain is a sensory experience distinct from sensations of touch, pressure, heat and cold. It is often described by sufferers by such terms as bright, dull, aching, pricking, cutting or burning and is generally considered to include both the original sensation and the reaction to that sensation. This range of sensations, as well as the variation in perception of pain by different individuals, renders a precise definition of pain difficult, however, many individuals suffer with severe and continuous pain.

Pain that is caused by damage to neural structures is often manifest as a neural supersensitivity or hyperalgesia and is termed "neuropathic" pain. Pain can also be "caused" by the stimulation of nociceptive receptors and transmitted over intact neural pathways, such pain is termed "nociceptive" pain.

The level of stimulation at which pain becomes noted is referred to as the "pain threshold." Analgesics are pharmaceutical agents which relieve pain by raising the pain threshold without a loss of consciousness. After administration of an analgesic drug a stimulus of greater intensity or longer duration is required before pain is experienced. In an individual suffering from hyperalgesia an analgesic drug may have an anti-hyperalgesic effect. In contrast to analgesics, agents such as local anaesthetics block transmission in peripheral nerve fibers thereby blocking awareness of pain. General anaesthetics, on the other hand, reduce the awareness of pain by producing a loss of consciousness.

Tachykinin antagonists have been reported to induce antinociception in animals, which is believed to be analogous to analgesia in man (Maggi et al, J. Auton. Pharmacol. (1993) 13, 23–93). In particular, non-peptide NK-1 receptor antagonists have been shown to produce such analgesia. For example, the NK-1 receptor antagonist RP 67,580 produced analgesia with potency comparable to that of morphine (Garret et al, Proc. Natl. Acad. Sci. USA (1993) 88, 10208–10212).

The opioid analgesics are a well-established class of analgesic agents with morphine-like actions. Synthetic and semi-synthetic opioid analgesics are derivatives of five chemical classes of compound: phenanthrenes; phenylheptylamines; phenylpiperidines; morphinans; and benzomorphans. Pharmacologically these compounds have diverse activities, thus some are strong agonists at the opioid receptors (e.g. morphine); others are moderate to mild agonists (e.g. codeine); still others exhibit mixed agonist-antagonist activity (e.g. nalbuphine); and yet others are partial agonists (e.g. nalorphine). Whilst an opioid partial agonist such as nalorphine, (the N-alkyl analogue of morphine) will antagonize the analgesic effects of morphine, when given alone it can be a potent analgesic in its own right.

Of all of the opioid analgesics, morphine remains the most widely used, but, in addition to its therapeutic properties, it has a number of drawbacks including respiratory depression, decreased gastrointestinal motility (resulting in constipation), nausea and vomiting. Tolerance and physical dependence also limit the clinical uses of opioid compounds.

Aspirin and other salicylate compounds are frequently used in treatment to interrupt amplification of the inflammatory process in rheumatoid diseases and arthritis and temporarily relieve the pain. Other drug compounds used for these purposes include phenylpropionic acid derivatives such as Ibuprofen and Naproxen, Sulindac, phenyl butazone, corticosteroids, antimalarials such as chloroquine and hydroxychloroquine sulfate, and fenemates (J. Hosp. Pharm., 36:622 (May 1979)). These compounds, however, are ineffective for neuropathic pain.

Available therapies for pain also have drawbacks. Some therapeutic agents require prolonged use before an effect is experienced by the patient. Other existing drugs have serious side effects in certain patients, and subjects must be carefully monitored to ensure that any side effects are not unduly threatening. Most existing drugs provide only temporary relief from pain and must be taken consistently on a daily or weekly basis. With disease progression the amount of medication needed to alleviate the pain often increases, thus increasing the potential for adverse side effects.

NMDA receptors are defined by the binding of N-methyl-D-aspartate (NMDA) comprise a receptor/ion channel complex with several different identified binding domains. NMDA itself is a molecule structurally similar to glutamate (Glu) which binds at the glutamate binding suite and is highly selective and potent in activating the NMDA receptor (Watkins (1987); Olney (1989)).

Many compounds are known that bind at the NMDA/Glu binding site (for example CPP, DCPP-ene, CGP 40116, CGP 37849, CGS 19755, NPC 12626, NPC 17742, D-AP5, D-AP7, CGP 39551, CGP-43487, MDL-100,452, LY-274614, LY-233536, and LY233053). Other compounds, referred to as non-competitive NMDA antagonists, bind at other sites in the NMDA receptor complex (examples are phencyclidine, dizocilpine, ketamine, tiletamine, CNS 1102, dextromethorphan, memantine, kynurenic acid, CNQX, DNQX, 6,7-DCQX, 6,7-DCHQC, R(+)-HA-966, 7-chloro-kynurenic acid, 5,7-DCKA, 5-iodo-7-chloro-kynurenic acid, MDL-28,469, MDL-100,748, MDL-29,951, L-689,560, L-687,414, ACPC, ACPCM, ACPCE, arcaine, diethylenetriamine, 1,10-diaminodecane, 1,12-diaminododecane, ifenprodil, and SL-82.0715). These compounds have been extensively reviewed by Rogawski (1992) and Massieu et. al., (1993), and articles cited therein.

In addition to its physiological function, glutamate (Glu) can be neurotoxic. Glu neurotoxicity is referred to as "excitotoxicity" because the neurotoxic action of Glu, like its beneficial actions, is mediated by an excitatory process (Olney (1990); Choi (1992)). Normally, when Glu is released at a synaptic receptor, it binds only transiently and is then rapidly removed from the receptor by a process that transports it back into the cell. Under certain abnormal conditions, including stroke, epilepsy and CNS trauma, Glu uptake fails and Glu accumulates at the receptor resulting in a persistent excitation of electrochemical activity that leads to the death of neurons that have Glu receptors. Many neurons in the CNS have Glu receptors, so excitotoxicity can cause an enormous amount of CNS damage.

Acute excitotoxicity injury can occur as a result of ischemic events, hypoxic events, trauma to the brain or spinal cord, certain types of food poisoning which involve an excitotoxic poison such as domoic acid, and seizure-mediated neuronal degeneration, which can result from persistent epileptic seizure activity (status epilepticus). A large body of evidence has implicated the NMDA receptor as one receptor subtype through which Glu mediates a substantial amount of CNS injury, and it is well established that NMDA antagonists are effective in protecting CNS neurons against excitotoxic degeneration in these acute CNS injury syndromes (Choi (1988); Olney (1990)).

In addition to neuronal damage caused by acute insults, excessive activation of Glu receptors may also contribute to more gradual neurodegenerative processes leading to cell death in various chronic neurodegenerative diseases, including Alzheimer's disease, amyotrophic lateral sclerosis, AIDS dementia, Parkinson's disease and Huntington's disease (Olney (1990)). It is generally considered that NMDA antagonists may prove useful in the therapeutic management of such chronic diseases.

In the 1980's it was discovered that PCP (also known as "angel dust") acts at a "PCP recognition site" within the ion channel of the NMDA Glu receptor. PCP acts as a non-competitive antagonist that blocks the flow of ions through the NMDA ion channel. More recently it has become evident that drugs which act at the PCP site as non-competitive NMDA antagonists are likely to have psychotomimetic side effects. Further, it is now recognized that certain competitive and non-competitive NMDA antagonists can cause similar pathomorphological effects in rat brain (Olney et. al., (1991); Hargreaves et. al., (1993)). Such compounds also have psychotomimetic effects in humans (Kristensen et. al., (1992); Herrling (1994); Grotta (1994)).

The glycine binding site of the NMDA receptor complex is distinguishable from the Glu and PCP binding sites. Also, it has recently been discovered that NMDA receptors occur as several subtypes which are characterized by differential properties of the glycine binding site of the receptor. Many compounds that bind at the NMDA receptor glycine site, useful for the treatment of stroke and neurodegenerative conditions, have been described in U.S. Pat. Nos. 5,604,227; 5,733,910; 5,599,814; 5,593,133; 5,744,471; 5,837,705 and 6,103,721.

SUMMARY OF THE INVENTION

It has now been discovered that certain compounds which exhibit the property of binding to the NMDA receptor glycine site have utility for the amelioration of pain and particularly for the amelioration of neuropathic pain.

In a first aspect the invention provides compounds according to structural diagram I useful for the treatment of pain,

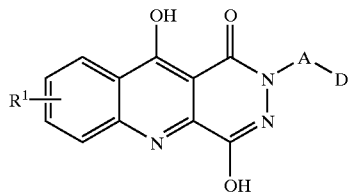

I wherein $R^1$ is halo; A is $(CH_2)_n$ where n is a value selected from 1, 2, 3 and 4; D is a five-membered heteroaryl moiety or a benz-derivative thereof, said heteroaryl moiety having one or two heteroatoms selected from oxygen, nitrogen and sulfur and having one or two substituents thereon, and substituents on moiety D are selected from $C_{1-4}$alkyl, phenyl, halo-substituted phenyl, halo, carboxy and $C_{1-4}$alkoxycarbonyl.

Other compounds useful in the methods and compositions of the invention are pharmaceutically-acceptable salts of the compounds in accord with structural diagram I and tautomers of such compounds.

Particular embodiments of the invention are those compounds wherein n is a value selected from 1 and 2, and substituents on moiety D are selected from $C_{1-2}$alkyl, halo-substituted phenyl, halo, carboxy and $C_{1-2}$alkoxycarbonyl.

More particular embodiments of the invention are those according to structural diagram II,

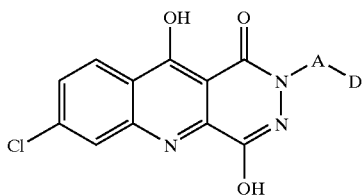

II wherein A and D are as defined for compounds of structural diagram I.

Further particular embodiment of the inventions are those according to structural diagram II wherein n is a value selected from 1 and 2, and substituents on moiety D are selected from $C_{1-2}$alkyl, halo-substituted phenyl, halo, carboxy and $C_{1-2}$alkoxycarbonyl.

Still more particular embodiments of the invention are those according to structural diagram II wherein n is 1, and substituents on moiety D are selected from methyl, chloro-substituted phenyl, halo and methoxycarbonyl.

The most particular embodiments of the invention are those exemplary compounds disclosed herein.

In another aspect the invention provides a method for the treatment of pain comprising administering a pain-ameliorating effective amount of any compound according to structural diagram I as defined heretofore.

In particular embodiments the method comprises administering pain-ameliorating effective amounts of compounds according to structural diagram I wherein n is a value selected from 1 and 2, and substituents on moiety D are selected from $C_{1-2}$alkyl, halo-substituted phenyl, halo, carboxy and $C_{1-2}$alkoxycarbonyl.

In more particular embodiments the method comprises administering a pain-ameliorating effective amount of a compound according to structural diagram I wherein n is 1, and substituents on moiety D are selected from methyl, chloro-substituted phenyl, halo and methoxycarbonyl.

Yet more particular embodiments are those where the method comprises treatment with compounds in accord with structural diagram II as defined heretofore.

Still more particular embodiments of the invention are those where the method comprises treatment with an exemplary compound specifically disclosed herein.

Another aspect of the invention is a method for making compounds in accord with structural diagram I.

Yet other aspects of the invention are pharmaceutical compositions which contain a compound in accord with structural diagram I; the use of compounds in accord with structural diagram I for the preparation of medicaments and pharmaceutical compositions, and a method comprising binding a compound of the invention to the NMDA receptor glycine site of a warm-blooded animal, such as a human being, so as to beneficially inhibit the activity of the NMDA receptor.

DETAILED DESCRIPTION OF THE INVENTION

Compounds of the invention are those within the scope of the generic description and particularly those compounds exemplified hereafter.

Suitable pharmaceutically-acceptable salts of compounds of the invention include acid addition salts such as methanesulphonate, fumarate, hydrochloride, hydrobromide, citrate, tris(hydroxymethyl)aminomethane, maleate and salts formed with phosphoric and sulphuric acid. In other embodiments, suitable salts are base salts such as an alkali metal salts for example sodium, alkaline earth metal salts for example calcium or magnesium, organic amine salts for example triethylamine, morpholine, N-methylpiperidine, N-ethylpiperidine, procaine, dibenzylamine, choline, N,N-dibenzylethylamine or amino acids such as lysine.

Another aspect of the invention is a process for making compounds of the invention, which process comprises the following steps:

a) Preparing a Boc-protected hydrazine by reacting an aldehyde, according to one of the procedures shown in the following scheme:

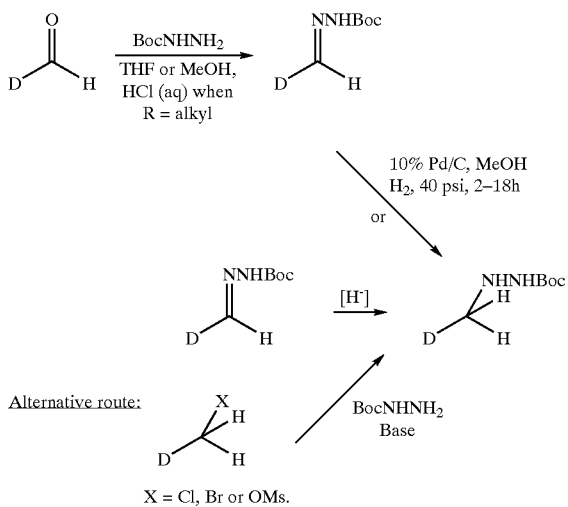

b) coupling said Boc-protected hydrazine and cyclizing the product according to the process of the following scheme to form a compound according to structural diagram I:

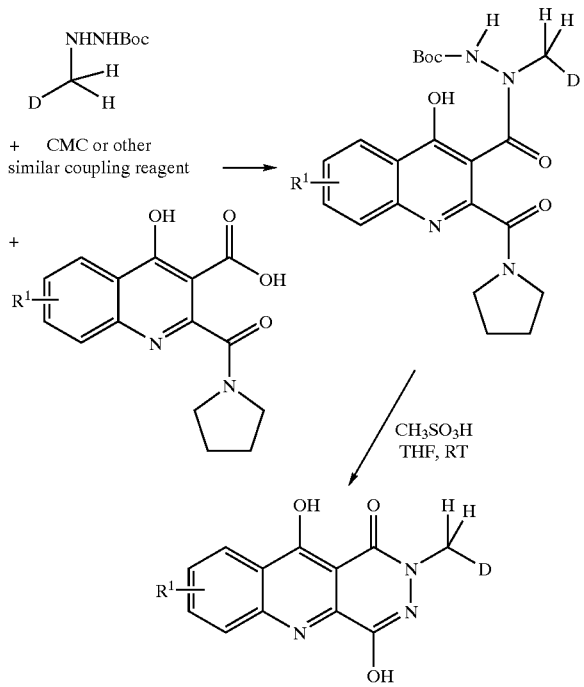

wherein:
CMC is 1-cyclohexyl-3-(2-morpholinoethyl) carbodiimide metho-p-toluenesulfonate;

the "R/H/D" group is the -A-D moiety of structural diagram I;
and throughout the foregoing process:
$R^1$ is as defined for structural diagram I.

To use a compound of the invention or a pharmaceutically-acceptable salt thereof for the therapeutic treatment, which may include prophylactic treatment, of pain in mammals, which may be humans, the compound can be formulated in accordance with standard pharmaceutical practice as a pharmaceutical composition.

Suitable pharmaceutical compositions that contain a compound of the invention may be administered in conventional ways, for example by oral, topical, parenteral, buccal, nasal, vaginal or rectal administration or by inhalation. For these purposes a compound of the invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions. A preferred route of administration is orally by tablet or capsule.

In addition to a compound of the present invention a pharmaceutical composition of this invention may also contain one or more other pharmacologically-active agents, or such pharmaceutical composition may be simultaneously or sequentially co-administered with one or more other pharmacologically-active agents.

Pharmaceutical compositions of this invention will normally be administered so that a pain-ameliorating effective daily dose is received by the subject. The daily dose may be given in divided doses as necessary, the precise amount of the compound received and the route of administration depending on the weight, age and sex of the patient being treated and on the particular disease condition being treated according to principles known in the art. A preferred dosage regime is once daily.

A further embodiment of the invention provides a pharmaceutical composition which contains a compound of the structural diagram I as defined herein or a pharmaceutically-acceptable salt thereof, in association with a pharmaceutically-acceptable additive such as an excipient or carrier.

A yet further embodiment of the invention provide the use of a compound of the structural diagram I, or a pharmaceutically-acceptable salt thereof, in the manufacture of a medicament useful for binding to the NMDA receptor glycine site in a warm-blooded animal such as a human being.

Still another embodiment of the invention provides a method of binding a compound of the invention to the NMDA receptor glycine site of a warm-blooded animal, such as a human being, in need of treatment for pain, which method comprises administering to said animal an effective amount of a compound of structural diagram I or a pharmaceutically-acceptable salt thereof.

Definitions:
When used herein the term "alkyl" includes both straight and branched chain alkyl groups but references to individual alkyl groups such as "propyl" refer to the straight chain moiety.

When used herein the term "halo" means fluoro, chloro, bromo and iodo.

When used herein the term "aryl" means an unsaturated carbon ring or a benz-derivative thereof. Particularly, aryl means phenyl, naphthyl or biphenyl. More particularly aryl means phenyl.

When used herein the term "heteroaryl" or "heteroaryl ring" means, unless otherwise further specified, a monocyclic-, bicyclic- or tricyclic-5–14 membered ring that is unsaturated or partially unsaturated, with up to five ring heteroatoms selected from nitrogen, oxygen and sulphur wherein a —CH$_2$— group can optionally be replaced by a —C(O)—, and a ring nitrogen atom may be optionally oxidized to form the N-oxide. Examples of such heteroaryls include thienyl, furyl, pyranyl, pyrrolyl, imidazolyl, pyrazolyl, thiazolyl, oxazolyl, isoxazolyl, pyridyl, pyridyl-N-oxide, oxopyridyl, oxoquinolyl, pyrimidinyl, pyrazinyl, oxopyrazinyl, pyridazinyl, indolinyl, benzofuranyl, benzimidazolyl, benzothiazolyl, quinolyl, isoquinolinyl, quinazolinyl, xanthenyl, quinoxalinyl, indazolyl, benzofuranyl and cinnolinolyl.

When used herein the term "heterocyclyl" or "heterocyclic ring" means, unless otherwise further specified, a mono- or bicyclic-5–14 membered ring, that is totally saturated, with up to five ring heteroatoms selected from nitrogen, oxygen and sulphur wherein a —CH$_2$— group can optionally be replaced by a —C(O)—. Examples of such heterocyclyls include morpholinyl, pyrrolidinyl, imidazolidinyl, pyrazolidinyl, piperidinyl, piperazinyl, homopiperidinyl, homopiperazinyl and quinuclidinyl.

When used herein, where optional substituents are selected from "one or more" groups it is to be understood that this encompasses compounds where all substituents are chosen from one of the specified groups and compounds where substituents are chosen from more than one of the specified groups.

Generally in the methods, processes and examples described herein:

concentrations were carried out by rotary evaporation in vacuo;

operations were carried out at ambient temperature, that is in the range 18–26° C. and under a nitrogen atmosphere;

column chromatography (by the flash procedure) was performed on Merck Kieselgel silica (Art. 9385) unless otherwise stated;

yields are given for illustration only and are not necessarily the maximum attainable;

the structure of the end-products of the formula I were generally confirmed by NMR and mass spectral techniques, proton magnetic resonance spectra were determined in DMSO-d$_6$ unless otherwise stated using a Varian Gemini 2000 spectrometer operating at a field strength of 300 MHz; chemical shifts are reported in parts per million downfield from tetramethylsilane as an internal standard (δ scale) and peak multiplicities are shown thus: s, singlet; bs, broad singlet; d, doublet; AB or dd, doublet of doublets; t, triplet, dt, double of triplets, m, multiplet; bm, broad multiplet; fast-atom bombardment (FAB) mass spectral data were obtained using a Platform spectrometer (supplied by Micromass) run in electrospray and, where appropriate, either positive ion data or negative ion data were collected, in this application, (M+H)$^+$ is quoted;

intermediates were not generally fully characterized and purity was in general assessed mass spectral (MS) or NMR analysis.

The following abbreviations and definitions when used, have the meanings, as follows:

| | |
|---|---|
| CDCl$_3$ | is deuterated chloroform; |
| CMC | is 1-cyclohexyl-3-(2-morpholinoethyl)carbodiimide metho-p-toluenesulfonate; |

-continued

| | |
|---|---|
| DCM | is dichloromethane; |
| DCU | is dicyclohexyl urea; |
| DHC | is 1,3-dicyclohexylcarbodiimide; |
| DMAP | is 4-(dimethylamino)pyridine; |
| DMF | is N,N-dimethylformamide; |
| DMSO | is dimethylsulphoxide; |
| m/s | is mass spectroscopy; |
| NMP | is N-methylpyrrolidinone; |
| NMR | is nuclear magnetic resonance; |
| p.o. | is per os; |
| THF | is tetrahydrofuran, and |
| t.i.d. | is three times daily. |

The examples and tests described herein are intended to illustrate but not limit the invention.

EXAMPLES

Example 1

7-Chloro-4-hydroxy-2-[3-(2,5-dimethyl)furanylmethyl]-1,2,5,10-tetrahydropyridazino[4,5-b]quinoline-1,10-dione.

2,5-dimethyl-3-furanmethanol.

To a 0° C. solution of methyl 2,5-dimethyl-3-furanoate (2.0 g, 13.0 mmol) in THF (130 mL) under N$_2$ was added lithium aluminum hydride (39 mL of a 1.0 M solution in THF, 38.9 mmol) dropwise. The reaction was stirred at 0° C. for 3.5 h, at which time it was quenched cautiously with saturated aqueous Na$_2$SO$_4$ solution and allowed to warm to room temperature. The reaction mixture was filtered and rinsed with ethyl acetate, the filtrate was diluted with more ethyl acetate and the layers separated. The organic layer was washed with saturated aqueous NH$_4$Cl, water and brine and dried over Na$_2$SO$_4$. The solution was filtered and concentrated to afford the title compound as a clear liquid (1.54 g, 12.2 mmol, 94%). $^1$H NMR (300 MHz, DMSO-d$_6$): δ 5.93 (s, 1H); 4.18 (s, 2H); 2.17 (s, 3H); 2.15 (s, 3H).

N'-(2,5-Dimethyl-furan-3-ylmethyl)-hydrazinecarboxylic acid tert-butyl ester.

To a 0° C. solution of 2,5-dimethyl-3-furanmethanol (750 mg, 5.95 mmol) in THF (60 mL) under N$_2$ was added phosphorus tribromide (169 mL, 1.78 mmol). After 0.5 hour, water was added and the solution was warmed to room temperature. The reaction was diluted with ethyl acetate and washed with saturated aqueous NaHCO$_3$, water and brine and dried over Na$_2$SO$_4$. It was then filtered and concentrated to afford a yellow-brown oil which was used in the following reaction without further purification.

To a stirred solution of 2,5-dimethyl-3-bromomethylfuran (5.95 mmol theor.) in DMF (30 mL) was added K$_2$CO$_3$ (1.64 g, 11.9 mmol) and tert-butylcarbazate (3.1 g, 23.8 mmol). The reaction was heated to 65° C. for 1 h. The reaction was cooled to room temperature, diluted with ethyl acetate and the layers separated. The organic layer was washed with saturated aqueous NH$_4$Cl, water and brine and dried over Na$_2$SO$_4$. The mixture was filtered, concentrated and distilled on a Kuglerohr apparatus at 100° C. and 35 mTorr to remove the excess DMF and tert-butylcarbazate. This material was then purified using silica gel column chromatography (hexanes—4:1 hexanes:ethyl acetate as eluant) to afford the title compound as a dark yellow oil (670 mg, 2.79 mmol, 47% for the two steps). $^1$H NMR (300 MHz, DMSO-d$_6$): δ 8.11 (br s, 1H); 5.91 (s, 1H); 4.38 (br s, 1H); 3.54 (s, 2H); 2.16 (s, 3H); 2.14 (s, 3H); 1.39 (s, 9H).

(tert-Butoxy)-N-[(2,4,6-trimethylphenyl)amino]carboxamide:

A suspension of 2,4,6-trimethylphenylhydrazine hydrochloride (15.02 g, 80.46 mmol) in saturated aqueous NaHCO$_3$ was stirred for 10 minutes and then treated with solid K$_2$CO$_3$ (18.97 g, 137.25 mmol). The resulting fine light yellow suspension was stirred for 10 minutes. A solution of di-tert-butyldicarbonate (25.03 g, 89.00 mmol) in 375 mL THF was added over 5 minutes and the resulting biphasic mixture was vigorously stirred for 3 hours. The reaction mixture was partitioned in water and the aqueous layer was extracted with diethyl ether (3×75 mL). The combined organic layers were washed with saturated NaCl (2×100 mL) and distilled water (2×100 mL), dried over $MgSO_4$, and concentrated under reduced pressure. Drying in vacuo afforded an orange oil which crystallized upon standing. The material was triturated in 5% diethyl ether in hexanes overnight to afford a beige solid which was isolated by filtration (13.82 g). The solid was recrystallized from diethyl ether/hexanes to afford 11.85 g (59%) of the desired product as a cream colored solid. The filtrates from the trituration and crystallization were combined and concentrated to afford 13.50 g of material which was purified by flash chromatography on silica gel using 25:75 diethyl ether:hexanes as eluant. This afforded an additional 4.69 g (23%) of the title compound. $^1$H NMR (300 MHz, $CDCl_3$): δ 6.79 (s, 2 H), 6.25 (bs, 1 H), 5.65 (bs, 1 H), 2.34 (s, 6 H), 2.22 (s, 3 H), 1.40 (s, 9 H); MS (CI) m/z 249.

Dimethyl 7-chloro-4-hydroxyquinoline-2,3-dicarboxylate:

A stirred mixture of methyl 2-amino-4-chlorobenzoate (2.50 g, 13.5 mmol) and dimethyl acetylenedicarboxylate (2.05 g, 14.4 mmol) in tert-butanol (22 ml) was refluxed for 7 hours under a nitrogen atmosphere. After adding additional dimethyl acetylenedicarboxylate (1.16 g, 8.13 mmol) and refluxing another 2.5 hours, the reaction mixture was allowed to cool to room temperature and potassium tert-butoxide (1.56 g, 13.9 mmol) was added in one portion. A precipitate formed and the resulting mixture was refluxed for 1.5 hours. The mixture was cooled to room temperature and filtered to separate the solids, which were washed with tert-butanol and diethyl ether. The solids were dissolved in water and acidified with 1 N sulfuric acid to form a precipitate. The resulting mixture was extracted with DCM and the combined extracts were washed with brine and water, dried over $MgSO_4$, filtered and concentrated to give a green solid. Recrystallization of this material from methanol provided the title compound (1.15 g, 47%) as an off-white solid, mp 232–233° C.; MS (CI): 296 (M+H). Analysis for $C_{13}H_{10}ClNO_5$: Calc'd: C, 52.81; H, 3.41; N, 4.74; Found: C, 52.75; H, 3.47; N, 4.69.

3-Carbomethoxy-7-chloro-4-hydroxyquinoline-2-carboxylic acid:

To a stirred suspension of dimethyl 7-chloro-4-hydroxyquinoline-2,3-dicarboxylate (1.0 g, 3.38 mmol) in water (20 mL) was added an aqueous solution of sodium hydroxide (0.27 g, 6.75 mmol). Upon addition, the suspension dissolved. The reaction mixture was warmed to 60° C. for 1 hour. After this time the reaction was cooled to room temperature and acidified with concentrated hydrochloric acid. The product was then extracted into diethyl ether and ethyl acetate. The organic extracts were dried over $MgSO_4$, filtered and concentrated in vacuo to provide the title compound as a solid (900 mg). This material was purified by recrystallization employing an ethyl acetate/hexane co-solvent system to provide the title compound (571 mg, 60%) as a white solid mp 296° C. (dec); MS (CI)=238 (M+H). Analysis for $C_{12}H_8NO_5Cl.0.45$ $CH_3CO_2CH_2CH_3.0.10$ $H_2O$: Calc'd: C, 51.30; H, 3.68; N 4.34, Found: C, 51.28; H, 3.62; N 3.97 $^1$H NMR 8.22 (d, J=8.7 Hz, 1H), 7.92 (d, J=1.8 Hz, 1H), 7.28 (dd, J=8.7, 1.8 Hz, 1H), 3.90 (s, 3H).

3-Carbomethoxy-2-pyrrolidinocarbamide-7-chloro-4-hydroxyquinoline:

To a suspension of 3-carbomethoxy-7-chloro-4-hydroxyquinoline-2-carboxylic acid (2.25 g, 8.0 mmol) in THF (20 mL) at ambient temperature under a $N_2$ atmosphere was added DHC (1.65 g, 8.0 mmol) and pyrrolidine (0.596 g, 8.4 mmol). The reaction was stirred room temperature for 15 hours after which time the by-product urea was removed via filtration. The desired product was purified via flash column chromatography employing 5% methanol in chloroform to provide the title compound (2.52 g, 94.3%) as a tan solid, mp=215° C.; MS (CI): 335 (M+H). 300 MHz $^1$H NMR (DMSO-$d_6$): δ 8.12 (d, J=8.7 Hz, 1H), 7.60 (d, 1H, J=1.8 Hz), 7.47 (dd, 1H, J=8.8, 2.0 Hz), 3.69 (s, 3H), 3.40–3.49 (m, 2H), 3.27–3.33 (m, 2H), 1.80–1.96 (m, 4H).

7-Chloro-4-oxo-2-(pyrrolidinylcarbonyl)hydroquinoline-3-carboxylic acid:

To a suspension of 3-carbomethoxy-2-pyrrolidinocarbamide-7-chloro-4-hydroxy quinoline (2.52 g, 7.5 mmol) in de-ionized water (40 mL) was added dropwise a solution (20 mL) of an aqueous potassium hydroxide (882 mg, 15.75 mmol). Upon complete addition, the reaction was warmed to 60° C. After 3 hours, the reaction was filtered to remove a small amount of insoluble material. The filtrate was then acidified to pH=1 which yield a white precipitate. The solid was isolated by vacuum filtration, washed with water, and dried at 30° C. in vacuo for 16 hours. This provided the title compound (1.5 g, 64%) as a white solid, mp=225–8° C.; MS (CI): 321 (M+H). 300 MHz $^1$H NMR (DMSO-$d_6$): δ 8.28 (d, J=8.8 Hz, 1H), 7.77 (s, 1H), 7.64 (d, 1H, J=8.7), 3.52–3.57 (m, 2H), 3.17–3.19 (m, 2H), 1.83–1.98 (m, 4H).

N'-[7-Chloro-4-oxo-2-(pyrrolidine-1-carbonyl)-1,4-dihydroquinoline-3-carbonyl]-N'-(2,5-dimethylfuran-3-ylmethyl)-hydrazinecarboxylic acid tert-butyl ester.

To a stirred slurry of 7-chloro-4-oxo-2-(pyrrolidinylcarbonyl)hydroquinoline-3-carboxylic acid (900 mg, 2.79 mmol) in THF (10 mL) was added CMC (2.36 g, 5.58 mmol). To this canary yellow mixture was added a solution of N'-(2,5-dimethyl-furan-3-ylmethyl)-hydrazinecarboxylic acid tert-butyl ester (670 mg, 2.79 mmol) and N,N-dimethyl-aminopyridine (51 mg, 420 mmol) in THF (20 mL). The resultant mixture was refluxed under $N_2$ for 3.5 h, then cooled and filtered. The filtrate was concentrated and filtered through a small column of silica gel ($CH_2Cl_{2-5}$% MeOH/$CH_2Cl_2$) to afford the title compound as a yellow solid; this material was used in the following reaction without further purification. MS m/z 543.2 (M+1)

7-Chloro-4-hydroxy-2-[3-(2,5-dimethyl)furanylmethyl]-1,2,5,10-tetrahydropyridazino[4,5-b]quinoline-1,10-dione.

To a stirred solution of N'-[7-chloro-4-oxo-2-(pyrrolidine-1-carbonyl)-1,4-dihydroquinoline-3-carbonyl]-N'-(2,5-dimethylfuran-3-ylmethyl)-hydrazinecarboxylic acid tert-butyl ester (2.79 mmol theor.) in THF (60 mL) was added methanesulfonic acid (7.25 mL, 112 mmol) dropwise. This solution was stirred at room temperature overnight, at which time water (ca. 150 mL) was added to induce precipitation of the product. The material was filtered to give a tan powder; this powder was dried at 30° C. under 500 mTorr overnight to afford the title compound as a tan powder (680 mg, 1.82 mmol, 66% for two steps). $^1$H NMR (300 MHz, DMSO-$d_6$): δ 12.51 (br s, 1H); 11.88 (br s, 1H); 8.14 (d, J=8.7 Hz, 1H); 8.01 (d, J=2.1 Hz, 1H); 7.42 (dd, J=1.8, 8.7 Hz, 1H); 5.94 (s, 1H); 4.79 (s, 2H); 2.27 (s, 3H); 2.14 (s, 3H). MS m/z 370.0 (M–1)

Example 2

7-Chloro-4-hydroxy-2-[2-(3-methyl)thienylmethyl]-2,5,10-tetrahydropyridazino[4,5-b]quinoline-1,10-dione.

(tert-Butoxy)-N-[1-aza-2-(3-methyl(2-thienyl)vinyl] carboxamide.

To a stirred solution of 3-methylthiophene-2-carboxaldehyde (5.03 g, 39.86 mmol) and absolute ethanol (75 mL) under nitrogen was added 3 drops of concentrated HCl, followed by the addition of tert-butylcarbazate (4.75 g, 35.94 mmol). After 30 minutes the reaction mixture was filtered and washed with ethanol (10 mL). The product was dried at 30° C. in vacuo to give the title compound as an off-white powder (6.92 g, 80% yield). H NMR (300 MHz, DMSO-$d_6$): δ 1.45 (s, 9H); 2.24 (s, 3H); 6.91 (d, 1H, J=5.1 Hz); 7.46 (d, 1H, J=5.1 Hz); 8.25 (s, 1H); 10.70 (s, 1H).

(tert-Butoxy)-N-{[(3-methyl(2-thienyl))methyl]amino}carboxamide.

To a stirred solution of (tert-butoxy)-N-[-aza-2-(3-methyl(2-thienyl)vinyl]carboxamide (2.60 g, 10.82 mmol) and dry THF (40 mL) under nitrogen was added p-toluene sulfonic acid monohydrate (2.09 g, 10.99 mmol) followed by sodium cyanoborohydride (1.78 g, 28.33 mmol). The reaction mixture was stirred at room temperature for 4 hours and then diluted with 2 N NaOH (40 mL). The resulting solution was extracted with ethyl acetate (3×40 mL) and the combined organic extracts were washed with brine (50 mL), then dried over $Na_2SO_4$. The $Na_2SO_4$ was filtered off and the filtrate was concentrated under reduced pressure to give an off-white solid (2.79 g). This product was purified by flash chromatography on silica gel eluting with hexane:ethyl acetate (3:1) to give the title compound as a colorless oil (2.44 g, 92% yield). $^1$H NMR (300 MHz, DMSO-$d_6$): δ 1.39 (s, 9H); 2.14 (s, 3H); 3.95 (d, 2H, J=4.5 Hz); 4.69 (d, 1H, J=3.9 Hz); 6.82 (d, 1H, J=5.1 Hz); 7.29 (d, 1H, J=5.1 Hz); 8.26 (s, 1H).

(tert-Butoxy)-N-{[7-chloro-4-hydroxy-2-(pyrrolidinylcarbonyl)(3-quinolyl)]-N-[(3-methyl(2-thienyl))methyl]carbonylamino}carboxamide.

To a stirred mixture of 7-chloro-4-oxo-2-(pyrrolidinylcarbonyl)hydroquinoline-3-carboxylic acid, Example 1, (3.56 g, 11.10 mmol) and dry THF (80 mL) under nitrogen was added CMC (7.11 g, 16.78 mmol). After stirring the reaction mixture for an additional 20 minutes, a solution of (tert-butoxy)-N-{[(3-methyl(2-thienyl))methyl]amino}carboxamide (2.44 g, 10.07 mmol) and THF (15 mL) was rapidly added. The mixture was heated to 70° C. and stirred overnight. The reaction was cooled to room temperature, filtered, and the filter cake was washed with THF (30 mL). The filtrate and washings were combined and concentrated under reduced pressure to give a yellow solid (6.72 g). The product was purified by flash chromatography on silica gel eluting with DCM:methanol (95:5) to give the desired compound (3.22 g, 59% yield) as a yellow powder.

7-Chloro-4-hydroxy-2-[2-(3-methyl)thienylmethyl]-1,2,5,10-tetrahydropyridazino[4,5-b]quinoline-1,10-dione.

To a stirred mixture of (tert-butoxy)-N-{[7-chloro-4-hydroxy-2-(pyrrolidinylcarbonyl)(3-quinolyl)]-N-[(3-methyl(2-thienyl))methyl]carbonylamino}carboxamide (3.68 g, 6.77 mmol) and dry THF (150 mL) under nitrogen was added methanesulfonic acid (10 mL, 14.8 g, 77.8 mmol) all at once. The mixture was stirred overnight and then concentrated under pressure. The residue was diluted with water (80 mL) and then filtered to separate the solids. The collected solids were successively washed with water (30 mL), methanol (20 mL), and diethyl ether (150 mL) and then dried at 50° C. in vacuo to give the title compound (1.98 g, 78% yield) as an off-white powder, m.p. >250° C. $^1$H NMR (300 MHz, DMSO-$d_6$): δ 2.32 (s, 3H), 5.17 (s, 2H); 6.84 (d, 1H, J=5.1 Hz); 7.32 (d, 1H, J=5.1 Hz); 7.43 (d, 1H, J=8.7 Hz); 8.02 (s, 1H); 8.14 (d, 1H, J=8.7 Hz); 11.92 (br s, 1H); 12.62 (br s, 1H). Calc'd. for $C_{17}H_{12}ClN_3O_3S.0.05 CH_3SO_3H.0.05 H_2O$: C, 54.62; H, 3.24; N, 11.24. Found: C, 53.96; H, 3.27; N, 11.07.

Example 3
7-Chloro-4-hydroxy-2-[(5-methyl(furan-2-yl))methyl]-1,2,5,10-tetrahydropyridazino[4,5-b]quinoline-1,10-dione.

The title compound was synthesized by the method of Example 2 using 5-methylfurfural as the starting material. $^1$H NMR (300 MHz, DMSO-$d_6$): δ 12.69 (br s, 1H); 11.92 (s, 1H); 8.43 (d, J=8.7 Hz, 1H); 8.02 (d, J=1.5 Hz, 1H); 7.43 (d, J=8.7 Hz, 1H); 6.22 (d, J=3.0 Hz, 1H); 6.01 (d, J=2.1 Hz, 1H); 5.02 (s, 2H); 2.21 (s, 3H). Calc'd. for $C_{17}H_{12}O_4N_3Cl.1.1 H_2O$: C, 54.08; H, 3.79; N, 11.13. Found: C, 53.99, 53.90; H, 3.69, 3.71; N, 11.05, 11.03.

Example 4
7-Chloro-4-hydroxy-2-[(2-methyl(furan-3-yl))methyl]-1,2,5,10-tetrahydropyridazino[4,5-b]quinonline-1,10-dione.

The title compound was prepared by the method of Example 1 using methyl 2-methyl-3-furoate as the starting material. $^1$H NMR (300 MHz, DMSO-$d_6$): δ 12.53 (br s, 1H); 11.89 (br s, 1H); 8.14 (d, J=8.7 Hz, 1H); 8.01 (d, J=1.8 Hz, 1H); 7.42 (m, 2H), 6.34 (d, J=1.5 Hz, 1H); 4.86 (s, 2H); 2.33 (s, 3H).

Example 5
7-Chloro-4-hydroxy-2-[3,5-dimethylisoxazol-4-yl)methyl]-1,2,5,10-tetrahydropyridazino[4,5-b]quinoline-1,10-dione.

The title compound was prepared by the method of Example 1 using 4-(chloromethyl)-3,5-dimethylisoxazole in place of 2,5-dimethyl-3-bromomethyl-furan as the starting material. $^1$H NMR (300 MHz, DMSO-$d_6$): δ 12.47 (br s, 1H); 11.89 (br s, 1H); 8.13 (d, J=8.7 Hz, 1H); 8.02 (d, J=1.8 Hz, 1H); 7.42 (d, J=7.5 Hz, 1H); 4.86 (s, 2H); 2.45 (s, 3H); 2.29 (s, 3H). Calc'd. for $C_{17}H_{13}O_4N_4Cl.1.0 H_2O$: C, 52.25; H, 3.87; N, 14.34. Found: C, 52.00, 51.92; H, 3.91, 3.91; N, 13.97, 13.93.

Example 6
7-Chloro-4-hydroxy-2-{[5-(2-chlorophenyl)(2-furyl)]methyl}-1,2,5,10-tetrahydropyridazino[4,5-b]quinoline-1,2-dione.

The title compound was synthesized by the method of Example 2 using 5-(2-chlorophenyl)-2-furfural as the starting material. $^1$H NMR (300 MHz, DMSO-$d_6$): δ 12.67 (s, 1H); 11.91 (s, 1H): 8.15 (d, J=8.7 Hz, 1H); 8.02 (d, J=1.5 Hz, 1H); 7.76 (dd, J=1.5, 7.8 Hz, 1H); 7.53 (d, J=7.8 Hz, 1H; 7.45–7.29 (m, 3H); 7.06(d, J=3.3 Hz, 1H); 6.15 (d, J=3.3 Hz, 1H); 5.18 (s, 2H). Calc'd. for $C_{22}H_{13}Cl_2N_3O_4$: C, 58.17; H, 2.89; N, 9.25; Found: C, 57.90, 57.83; H, 3.05, 3.06; N, 9.11, 9.08.

Example 7
7-Chloro-4-hydroxy-2-[(4,5-dimethyl(furan-2-yl))methyl]-1,2,5,10-tetrahydropyridazino[4,5-b]quinoline-1,10-dione.

The title compound was synthesized by the method of Example 2 using 4,5-dimethyl-2-furfural as the starting material. $^1$H NMR (300 MHZ, DMSO-$d_6$): δ 12.60 (s, 1H); 11.87 (s, 1H); 8.14 (d, J=8.7 Hz, 1H); 8.02 (d, J=1.8 Hz, 1H); 7.42 (dd, J=8.4, 1.5 Hz, 1H); 6.12 (s, 1H; 4.97 (s, 2H); 2.12 (s, 3H); 1.85 (s, 3H). Calc'd. for $C_{18}H_{14}ClN_3O_4.1.5 H_2O$: C, 54.21; H, 4.30; N, 10.54; Found: C, 54.09, 54.49; H, 4.13, 4.16; N, 10.45, 10.49.

Example 8
7-Chloro-4-hydroxy-2-(5-methoxycarbonyl(furan-2-yl)methyl)-1,2,5,10-tetrahydropyirdazino[4,5-b]quinolin-1,10-dione.

The title compound was synthesized by the method of Example 2 using methyul-5-formylfuran-carboxylate as the starting material. $^1$H NMR (300 MHz, DMSO-$d_6$): δ 12.75 (s, 1H); 11.91 (s, 1H); 8.14 (d, J=8.7 Hz, 1H); 8.13 (s, 1H); 7.43 (d, J=8.7 Hz, 1H); 7.26 (d, J=3.3, 1H); 6.57 (d, J=3.3 Hz, 1H); 5.16 (s, 2H); 3.77 (s, 3H). Calc'd. for $C_{18}H_{12}ClN_3O_6.0.05 CH_4SO_3$: C, 53.32; H, 3.03; N, 10.34; Found: C, 53.24, 53.24; H, 3.05, 3.04; N, 10.30, 10.29.

Example 9
7-Chloro-4-hydroxy-2-(5-methylthien-2-ylmethyl)-1,2,5,10-tetrahydropyridazino[4,5-b]quinoline-1,10-dione.

The title compound was synthesized by the method of Example 2 using 5-methylthiophene-2-carboxaldehyde as the starting material. $^1$H NMR (300 MHz, DMSO-$d_6$) δ 12.70 (s, 1 H); 11.92 (s, 1 H); 8.14 (d, J=8.9 Hz, 1 H); 8.01 (d, J=2.0 Hz, 1 H); 7.43 (dd, J=1.8, 8.8 Hz, 1 H); 6.87 (d, J=3.5 Hz, 1 H); 6.64 (d, J=2.3 Hz, 1 H); 5.13 (s, 2 H); 2.37 (s, 3 H).

Example 10
7-Chloro-4-hydroxy-2-(2-methylbenz[b]thien-2-ylmethyl)-1,2,5,10-tetrahydropyridazino[4,5-b]quinoline-1,10-dione.

The title compound was synthesized by the method of Example 2 using 3-methylbenzothiophene-2-carboxaldehyde as the starting material. $^1$H NMR (300 MHz, DMSO-$d_6$) δ 12.68 (s, 1 H); 11.94 (s, 1 H); 8.14 (d, J=8.7 Hz, 1 H); 8.02 (d, J=1.8 Hz, 1 H); 7.85 (d, J=7.2 Hz, 1 H); 7.74 (d, J=7.5 Hz, 1 H); 7.44–7.30 (m, 3 H); 5.34 (s, 2 H); 2.50 (s, 3 H).

Example 11
7-Chloro-4-hydroxy-2-(3-methyl-5-bromothien-2-ylmethyl)-1,2,5,10-tetrahydropyridazino[4,5-b]quinoline-1,10-dione.

Bromination of 3-methylthiophene-2-carboxaldehyde gave 4-bromo-3-methylthiophene-2-carboxaldehyde (reference: Spinelli, D.; Consiglio, G.; Corrao, A. *JCS Perkins II*, 1972, 1866). The title compound was then synthesized from this intermediate by the method of Example 2. $^1$H NMR (300 MHz, DMSO-$d_6$) δ 12.61 (br s, 1 H); 11.90 (br s. 1 H); 8.14 (d, J=8.7 Hz, 1 H); 8.02 (s, 1 H); 7.42 (d, J=8.4 Hz, 1 H); 6.95 (s, 1 H); 5.10 (s, 2 H); 2.28 (s, 3 H).

Example 12
7-Chloro-4-hydroxy-2-(4-methyl-imidazol-3-ylmethyl)-1,2,5,10-tetrahydropyridazino[4,5-b]quinoline-1,10-dione.

To a stirred slurry of 7-chloro-4-oxo-2-(pyrrolidinylcarbonyl)hydroquinoline-3-carboxylic acid, Example 1, (0.92 g, 2.89 mmol) in DCM (40 mL) was added 1-(3-dimethylaminopropyl)-3-ethylcarbodiimide hydrochloride (0.63 g, 3.32 mmol) and the reaction was stirred for five minutes. To this mixture was rapidly added, a solution of (tert-butoxy)-N-[(4-methyl-imidazol-3-ylmethyl)amino]carboxamide (0.68 g, 3.03 mmol, prepared in a manner analogous to (tert-butoxy)-N-{[(3-methyl(2-thienyl))methyl]amino}carboxamide, Example 2) and DMAP (0.02 g, 0.1 mmol) in DCM (10 mL), and the mixture was refluxed for four hours. The reaction was cooled, diluted with DCM (50 mL). The DCM was extracted with water (1×20 mL), sodium bicarbonate (sat. aqueous, 1×20 mL) and sodium chloride (sat. aqueous, 1×20 mL). The organic layer was dried over MgSO$_4$ and the solvent removed in vacuo to give the title compound as a yellow foam (1.3 g) which was used in the next reaction without further purification.

The final cyclization step was performed in a manner analogous to that described in Example 2. Yield 3%. $^1$H NMR (300 MHz, DMSO-$d_6$): δ 2.31 (CH$_3$SO$_3$H); 2.33 (s, 3H); 5.12 (s, 2H); 7.45 (d, 1H, J=8.7 Hz); 8.02 (s, 1H); 8.15 (d, 1H, J=8.7 Hz); 8.92 (s, 1H); 11.97 (br s, 1H); 14.13 (br s, 1H). MS (+CI) m/z 358/360.

Tests for Biological Function
Test A: Inhibition of Binding of [$^3$H]-MDL105,519:

Binding of compounds to the NMDA receptor glycine site may be assessed by measuring the ability of test compounds to inhibit the binding of tritiated MDL105,519 to brain membranes bearing the receptor.

Rat Brain Membranes: The rat brain membranes used in the experiments were obtained from Analytical Biological Services Inc., and were prepared substantially in accordance with the method of B. M. Baron et al., *J. Pharmacol. Exp. Ther.* 250, 162 (1989). Briefly, fresh brain tissue including cerebral cortex and hippocampus from male Sprague Dawley rats was homogenized in 0.32 M sucrose and centrifuged at low speed to separate cellular membranes from other cellular components. The membranes were then washed 3 times using deionized water, followed by treatment with 0.04% Triton X-100. Finally, membranes were washed six times in 50 mM Tris citrate buffer, pH 7.4, and frozen at −80° C. until use.

[$^3$H]MDL105,519 (72 Ci/mmol) was purchased from Amersham. Cold MDL105,519 was purchased from Sigma/RBI. Binding assays were performed substantially in accordance with the protocol of B. M. Baron et al., *J. Phannacol. Exp. Ther.* 279, 62 (1996), as follows. On the day of the experiment, brain membranes were thawed at room temperature and suspended in 50 mM tris acetate buffer, pH 7.4 ("TAB"). Seventy-five micro grams per milliliter protein (by using the BioRad dye) were used for competition binding. The experiments were carried out using 96-well plates. Membranes were incubated with 20 µL of compounds of various concentrations and 1.2 nM [$^3$H]MDL105,519 for 30 minutes at room temperature in a total volume of 250 µL. Non specific binding was determined by using 100 µM of unlabeled MDL105,519. The unlabeled MDL105,519 and compounds were dissolved as 12.5 mM stock solutions in DMSO. Final DMSO concentration in each well was kept below 1%, which concentration was found not to alter the binding results. After incubation, unbound [$^3$H]MDL105,519 was removed by filtration onto GF/B Unifilter plates using a Packard harvester. Filters were washed four times with ice cold TAB (total of 1.2 mL buffer). The plates were dried overnight at room temperature and bound radioactivity was measured on a Packard TopCount after the addition of 45 µL per well of the MICROSCINT O.

Human Brain Membranes: Human brain membranes were obtained from Analytical Biological Services Inc., and assays were performed as described for rat membranes.

Data analysis: Data was analyzed using a Microsoft Excel spreadsheet and GraphPad Prizm software and potency of compounds is expressed as the Ki (nM).

Test B: Formalin Test:

The Formalin test is an assay that assesses the capacity of a compound to inhibit formalin-induced nociceptive behaviors in rats (D. Dubuisson, et al., *Pain* 4, 161–174 (1977); H. Wheeler-Aceto et al., *Psychopharmacology* 104, 35–44 (1991); T. J. Coderre, et al., *Pain* 54, 43–50 (1993)). In the test, two distinctive phases of formalin-induced behaviors are observed. A first phase response, caused by acute nociception to the noxious chemical (formalin) injected into the paw, occurs between zero and five minutes. A quiescent period of 5 to 15 min post injection follows. After the quiescent period a second phase response, caused by sensitization of the central neurons in the dorsal horn, occurs after 15 minutes and lasts up to 60 minutes. Sensitization of the central neurons in the spine augments a noxious afferent input and causes a stronger pain barrage to be transmitted to the brain. Therefore, inhibition of the second phase response indicates a central mechanism of drug action.

The procedure for the formalin test may be performed as follows: male rats are placed in a plexiglass chamber and observed for 30–45 min. to observe their baseline activity. Animals would either be pretreated with vehicle or with different doses of a test compound and are dosed with vehicle or test compound three hours prior to injection of 0.05 mL of sterile 1% formalin under the dorsal skin of a hind paw. The number of paw flinches (responses) during the first phase (0–5 min.) and the second phase (20–35 min.)

are scored and recorded. Flinch response can be compared with the mean score of a saline control group and calculated as percentage inhibition. The $ED_{50}$ is the dose of compound which produced 50% inhibition of nociceptive response in the first or second phase response.

% inhibition of nociceptive response can be calculated as:

$$100 \times \frac{\text{(number of responses in vehicle group} - \text{number of responses in compound group)}}{\text{(number of responses in vehicle group)}}$$

Student's t-test can be used for statistical analysis to determine the significance of compound effects.

Test C: Neuropathic Pain Model (Chronic Constriction Injury):

The anti-hyperalgesic properties of a compound may be tested with the Chronic Constriction Injury ("CCI") model. The test is a model for neuropathic pain associated with nerve injuries that can arise directly from trauma and compression, or indirectly from a wide range of diseases such as infection, cancer, metabolic conditions, toxins, nutritional deficiencies, immunological dysfunction, and musculoskeletal changes. In the model a unilateral peripheral hyperalgesia is produced in rats by nerve ligation (G. J. Bennett, et al., *Pain* 33, 87–107 (1988)).

Procedurally, Sprague-Dawley rats (250–350 g) are anesthetized with sodium pentobarbital and the common sciatic nerve is exposed at the level of the mid thigh by blunt dissection through the biceps femoris. A section of nerve (about 7 mm), proximal to the sciatic trifucation, is freed of tissue and ligated at four positions with chromic gut suture. The suture is tied with about 1 mm spacing between ligatures. The incision is closed in layers and the animals are allowed to recuperate. Thermal hyperalgesia is measured using a paw-withdrawl test (K. Hargreaves, et al., *Pain* 32, 77–88 (1988)). To perform the test, animals are habituated on an elevated glass floor. A radiant heat source is aimed at the mid-plantar hindpaw (sciatic nerve territory) through the glass floor with a 20 second cut-off used to prevent injury to the skin. The latencies for the withdrawal reflex in both hind paws are recorded.

Injured paws with ligated nerves show shorter paw withdrawal latencies compared to the uninjured or sham operated paws. Responses to test compounds are evaluated at different times after oral administration to determine the onset and duration of compound effect. When performing the test, groups of CCI rats receive either vehicle or the test compound orally three times daily for 5 days. Paw withdrawal latencies are measured each day 10 min before and 2 or 3 hr. after the first daily dose. Compound efficacy is expressed as mean percentage decrease of hyperalgesia compared to that of vehicle-treated animals, calculated as follows:

$$\frac{\text{(Mean of vehicle group} - \text{Mean of compound group)}}{\text{(Mean of vehicle group)}} \times 100.$$

Data analysis was performed by the multiple means comparison test (Dunnett's test) and results are expressed and compound potencies are expressed as the MED (minimum effective dose), in mg/Kg/day, that yields a percent (%) decrease in hyperalgesia that is statistically significant.

Table 1 shows the results from Tests A and C for certain compounds of the invention. Where no data is provided in the table, the test was not performed.

TABLE 1

| Example No. | Test A Ki (nM)) | Test C MED (% Inh.) |
|---|---|---|
| Ex. 1 | 24.8 | |
| Ex. 2 | 12.7 | 30 (−15%) |
| Ex. 3 | 47 | |
| Ex. 4 | 28 | |
| Ex. 5 | 39 | |
| Ex. 6 | 298 | |
| Ex. 7 | 175 | |
| Ex. 8 | 72 | |
| Ex. 9 | 28 | |
| Ex. 10 | 161 | |
| Ex. 11 | 51 | |
| Ex. 12 | 434 | |

What is claimed is:

1. A compound according to formula I;

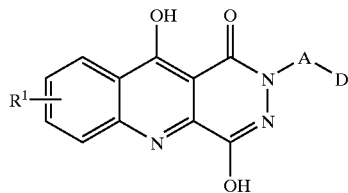

wherein:
$R^1$ is halo;
A is $(CH_2)_n$ where n is a value selected from 1, 2, 3 and 4;
D is a five-membered heteroaryl moiety or a benzo-fused-derivative thereof, said heteroaryl moiety having one or two heteroatoms selected from oxygen, nitrogen and sulfur and having one or two substituents thereon,
said substituents being selected from $C_{1-4}$alkyl, phenyl, halo-substituted phenyl, halo, carboxy and $C_{1-4}$alkoxycarbonyl,
or tautomers or pharmaceutically-acceptable salts thereof.

2. A compound according to claim 1, wherein:
n is a value selected from 1 and 2, and
said substituents are selected from $C_{1-2}$alkyl, halo-substituted phenyl, halo, carboxy and $C_{1-2}$alkoxycarbonyl.

3. A compound of claim 1, according to formula II,

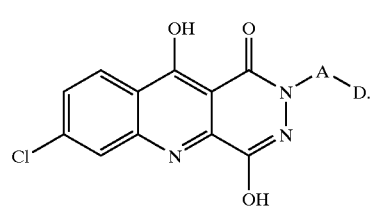

4. A compound according to claim 3, wherein:
n is a value selected from 1 and 2, and
said substituents are selected from $C_{1-2}$alkyl, halo-substituted phenyl, halo, carboxy and $C_{1-2}$alkoxycarbonyl.

5. A compound according to claim 4, wherein:
n is 1, and
said substituents are selected from methyl, chloro-substituted phenyl, halo and methoxycarbonyl.

6. A compound according to claim 1, selected from:
7-chloro-4-hydroxy-2-[2,5-dimethyl(3-furanyl)]methyl-1,2,5,10-tetrahydropyridazino[4,5-b]quinoline-1,10-dione;
7-chloro-4-hydroxy-2-[(3-methyl(2-thienyl))methyl]-1,2,5,10-tetrahydropyridazino[4,5-b]quinoline-1,10-dione;
7-chloro-4-hydroxy-2-(5-methylfuran-2-ylmethyl)-1,2,5,10-tetrahydropyridazino[4,5-b]quinoline-1,10-dione;
7-chloro-4-hydroxy-2-[2-methylfuran-3-yl]methyl-1,2,5,10-tetrahydropyridazino[4,5-b]quinoline-1,10-dione;
7-chloro-4-hydroxy-2-(4-(3,5-dimethyl)isoxazolino)methyl-1,2,5,10-tetrahydropyridazino[4,5-b]quinoline-1,10-dione;
7-chloro-4-hydroxy-2-(5-(2-chlorophenyl)furan-2-ylmethyl)-1,2,5,10-tetrahydropyridazino[4,5-b]quinoline-1,10-dione;
7-chloro-4-hydroxy-2-(4,5-dimethylfuran-2-ylmethyl)-1,2,5,10-tetrahydropyridazino[4,5-b]quinoline-1,10-dione;
7-chloro-4-hydroxy-2-(5-methylcarboxyfuran-2-ylmethyl)-1,2,5,10-tetrahydropyridazino[4,5-b]quinoline-1,10-dione;
7-chloro-4-hydroxy-2-(5-methylthien-2-ylmethyl)-1,2,5,10-tetrahydropyridazino[4,5-b]quinoline-1,10-dione;
7-chloro-4-hydroxy-2-(2-methylbenz[b]thien-2-ylmethyl)-1,2,5,10-tetrahydropyridazino[4,5-b]quinoline-1,10-dione, and
7-chloro-4-hydroxy-2-(3-methyl-5-bromothien-2-ylmethyl)-1,2,5,10-tetrahydropyridazino[4,5-b]quinoline-1,10-dione.

7. A method for treating a subject suffering from pain comprising administering a pain-ameliorating effective amount of a compound according to formula I

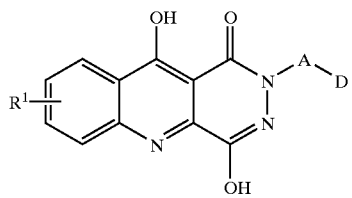

wherein:
$R^1$ is halo;
A is $(CH_2)_n$ where n is a value selected from 1, 2, 3 and 4;
D is a five-membered heteroaryl moiety or a benzo-fused-derivative thereof, said heteroaryl moiety having one or two heteroatoms selected from oxygen, nitrogen and sulfur and having one or two substituents thereon,
said substituents being selected from $C_{1-4}$alkyl, phenyl, halo-substituted phenyl, halo, carboxy and $C_{1-4}$alkoxycarbonyl,
or tautomers or pharmaceutically-acceptable salts thereof.

8. A method according to claim 7, wherein in said compound according to formula I:
n is a value selected from 1 and 2, and
said substituents are selected from $C_{1-2}$alkyl, halo-substituted phenyl, halo, carboxy and $C_{1-2}$alkoxycarbonyl.

9. A method according to claim 8, wherein in said compound according to formula I:
n is 1, and
said substituents are selected from methyl, chloro-substituted phenyl, halo and methoxycarbonyl.

10. A pharmaceutical composition comprising a pain-ameliorating effective amount of a compound according to formula I together with a pharmaceutically-acceptable excipient or diluent;

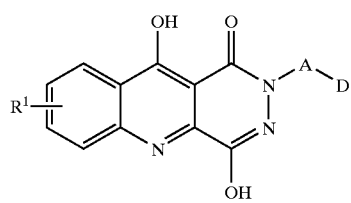

wherein:
$R^1$ is halo;
A is $(CH_2)_n$ where n is a value selected from 1, 2, 3 and 4;
D is a five-membered heteroaryl moiety or a benzo-fused-derivative thereof, said heteroaryl moiety having one or two heteroatoms selected from oxygen, nitrogen and sulfur and having one or two substituents thereon,
said substituents being selected from $C_{1-4}$alkyl, phenyl, halo-substituted phenyl, halo, carboxy and $C_{1-4}$alkoxycarbonyl,
or tautomers or pharmaceutically-acceptable salts thereof.

* * * * *